United States Patent
Perkins

(10) Patent No.: US 6,692,974 B2
(45) Date of Patent: Feb. 17, 2004

(54) ANALYTICAL APPARATUS

(75) Inventor: Elaine A Perkins, Salisbury (GB)

(73) Assignee: The Secretary of State for Defence in Her Brittanic Majesty's Government of the United Kingdom of Great Britain and Northern Ireland, Farnborough (GB)

(*) Notice: Subject to any disclaimer, the term of this patent is extended or adjusted under 35 U.S.C. 154(b) by 396 days.

(21) Appl. No.: 09/885,538

(22) PCT Filed: Nov. 5, 1997

(86) PCT No.: PCT/GB97/03037
§ 371 (c)(1),
(2), (4) Date: Nov. 16, 1996

(87) PCT Pub. No.: WO98/22808
PCT Pub. Date: May 28, 1998

(65) Prior Publication Data
US 2002/0016011 A1 Feb. 7, 2002

Related U.S. Application Data

(62) Division of application No. 09/308,501, filed on May 7, 1999, now Pat. No. 6,268,125.

(30) Foreign Application Priority Data
Nov. 16, 1996 (GB) .............................................. 9623820

(51) Int. Cl.[7] ............................................ G01N 33/543
(52) U.S. Cl. ..................... 436/518; 356/317; 356/318; 356/320; 385/12; 385/129; 385/130; 422/55; 422/57; 422/68.1; 422/82.11; 435/7.1; 435/287.1; 435/287.2; 435/287.9; 435/288.7; 435/808; 436/164; 436/165; 436/524; 436/525; 436/805
(58) Field of Search ................................ 356/317, 318, 356/320; 385/12, 129, 130; 422/55, 57, 68.1, 82.11; 435/7.1, 287.1, 287.2, 287.9, 288.7, 808, 5; 436/164, 165, 518, 524, 525, 805

(56) References Cited

U.S. PATENT DOCUMENTS 4,810,658 A * 3/1989 Shanks et al. ............... 436/172
4,844,613 A * 7/1989 Batchelder et al. .......... 356/318

(List continued on next page.)

FOREIGN PATENT DOCUMENTS

WO    WO 90 05295 A    5/1990

OTHER PUBLICATIONS

Peterlinz K A et al: "Two–Color Approach for Determination of Thickness and Dielectric Constatn of Thin Films Using Surface Plasmon Resonance Spectroscopy" Optics Communications, vol. 130, No. 4/06, Oct. 1, 1996, pp. 260–266, XP000627753 see figure 2.

*Primary Examiner*—Christopher L. Chin
(74) *Attorney, Agent, or Firm*—Nixon & Vanderhye P.C.

(57) ABSTRACT

A surface plasmon resonance apparatus for detecting a soluble analyte (e.g. a protein) or a particulate analyte (e.g. a cell), the apparatus comprising: (a) a sensor block adapted to receive a sensor, said sensor, for example a sensor slide, having a metallized sensor surface capable of binding the analyte; (b) a light source capable of generating an evanescent wave at the sensor surface of a sensor slide on the sensor block; (c) a first detector capable of detecting light from the light source which is internally reflected from the sensor surface; and (d) a second detector (e.g. a video camera) capable of detecting light scattered or emitted from an analyte bound thereto. Optionally the apparatus further comprises a second light source for increasing the intensity of the light scattered or emitted from an analyte bound to the sensor surface, preferably, this is sited to such as to minimize the amount of light transmitted therefrom which is detected by the first detector. Also disclosed are sensors adapted for use in the apparatus, and methods of detecting analytes in samples comprising exposing samples to the sensor surface of the apparatus.

4 Claims, 3 Drawing Sheets

U.S. PATENT DOCUMENTS

| | | | |
|---|---|---|---|
| 4,889,427 A | * 12/1989 | Van Veen et al. | 356/445 |
| 4,978,503 A | * 12/1990 | Shanks et al. | 422/58 |
| 5,023,053 A | * 6/1991 | Finlan | 422/82.05 |
| 5,242,828 A | * 9/1993 | Bergstrom et al. | 435/808 |
| 5,341,215 A | * 8/1994 | Seher | 356/445 |
| 5,437,940 A | 8/1995 | Hilston et al. | |
| 5,485,277 A | 1/1996 | Foster | |
| 5,492,840 A | * 2/1996 | Malmqvist et al. | 436/518 |
| 5,846,843 A | * 12/1998 | Simon | 385/12 |

* cited by examiner

ANALYTICAL APPARATUS

This application is a division of application Ser. No. 09/308,501, filed May 7, 1999, now U.S. Pat. No. 6,268,125 the entire content of which is hereby incorporated by reference in this application and which is a 371 of PCT GB97/03037 filed Nov. 5, 1997.

TECHNICAL FIELD

The present invention relates broadly to apparatus for the detection of analytes. The invention further relates to methods employing such apparatus.

BACKGROUND ART

The use of Surface Plasmon Resonance (SPR) for the detection of small soluble analytes from solution is well known (see e.g. "Advances in Biosensors—A Research Annual Vol 1. 1991" Ed. A P F Turner, Pub. Jai Press Ltd, London).

Briefly, an SPR apparatus generally comprises a light source for generating polarised light; a sensor, the outside of which is metal coated and may be contacted with a sample solution, and means for detecting the light which is internally reflected from the inner sensor surface.

In the absence of bound analyte, light is totally internally reflected at an incident angle characteristic of the refractive index (RI) of the sensor and of the sample solution. At a particular incident angle (the 'SPR angle'), interaction of the metal with the evanescent wave set up by internal reflection of the polarised light causes a drop in intensity of the reflected light. This drop can be observed using the light detector.

The binding of analyte to the sensor surface, within the evanescent wave zone, alters the RI of the sensor and this perturbs the SPR angle. This perturbation can be observed using the light sensor and related to the surface concentration of analyte.

SPR detection in the literature has generally been limited to use with soluble molecular size analytes e.g. biomolecules such as proteins and nucleic acids which are specifically bound within the evanescent zone using appropriate ligands.

However, the SPR apparatus in the art to date has not been suitable for accurately detecting sample materials with both soluble and insoluble analytes therein. In particular, due to the more limited way in which (for instance) roughly spherical cells of several $\mu$m diameter interact with the evanescent zone, only fairly high concentrations (e.g. $10^7$–$10^8$/ml) have been detectable using SPR. Thus in order to detect cells, as opposed to (for instance) protein antigens, further apparatus, and hence more cost, time and experimentation, have been required. For instance cells have frequently been detected using culture techniques followed by specific detection.

DISCLOSURE OF THE INVENTION

1. A surface plasmon resonance apparatus for detecting single particulate analytes, the apparatus comprising:
   (a) a sensor, or means to receive a sensor, said sensor providing a metallised surface capable of binding the analyte;
   (b) a light source capable of generating an evanescent wave at the sensor surface;
   (c) a detector capable of detecting light scaterered or emitted from a single particulate analyte bound at the sensor surface, said detector being located on the opposite side of the sensor surface to which light from said source is incident.

Suitable sensors are slides.

Possible analytes may include those particulate or insoluble analytes containing or consisting of biomolecules, for instance bacteria or other cells, spores, viruses or virions etc., or biomolecules themselves such as proteins or polynucleotides. Possible bacterial targets include *cryptosporidium, E. coli, salmonella* etc.

The apparatus may thus be used with a wide variety of samples suspected or known to contain analytes. For examples environmental samples such as water, or biological samples.

Broadly speaking the apparatus operates as follows: in use the second detector detects the binding of soluble analytes to the sensor surface by detecting the changes in the intensity of light internally reflected from the sensor surface, whereas the first detector detects the binding of particulate analytes to the sensor surface by detecting the light scattered or emitted from the analytes bound thereto. The apparatus of the present invention is therefore capable of the sensitive detection of both soluble and particulate analytes, and thus may provide a quicker, cheaper or more sensitive alternative to the methods and apparatus presently used in the art.

It is important to stress the different functions of the detectors in the apparatus. The second detector must be arranged to detect light internally reflected from the sensor surface, the intensity of this light being dependent on the SPR effects occurring as analytes (especially soluble ones) bind at the sensor surface altering the refractive index of the sensor/sample interface. The detector may be a 2-D array detector as described in more detail in the Examples below.

By contrast the fist detector detects light which is scattered or otherwise emitted (optionally by fluorescence) from analytes (especially particulate ones) which interact with the evanescent field at the sensor surface. This may give a sensitivity for detecting large particulate analytes several orders of magnitude higher than would be obtainable using pure SPR. Clearly the nature of the first detector used will determine the sensitivity and acuity of the detection, but in preferred embodiments single cells bound within the evanescence zone may be detected and resolved using the first detector while the bulk binding effects of soluble molecules may be detected using the first.

Preferably the first detector is a video camera (e.g. a Charge Coupled Detector [CCD] camera), but any kind of light detector appropriated for detecting light scattered or emitted from the analytes may be used e.g. a 2-D diode array, a photomultiplier etc.

In one embodiment the first detector is located on the same side of the surface as the light source such as to be capable of detecting light which is back-scattered or emitted when an analyte is bound to thereto.

The term 'light source' as used herein means any source of light radiation, including where appropriate the tip of an optical fibre which is attached to a remote radiation source.

In a different embodiment, the first detector is located on the opposite side of the surface as the light source detector such as to be capable of detecting light which is scattered or emitted when an analyte is bound to thereto.

In either case it may be desirable that the first detector is located such as to be capable of detecting light scattered or emitted at a predetermined angle, for example substantially normally, to the sensor surface. This will minimise interference from light which is being totally internally reflected from the surface.

Generally the sensor block will comprise a prism or a hemicylinder, such as are known to those skilled in the art of SPR detection. The sensor block is adapted to receive the detachable sensor which provides the metallised surface. The adaptation may simply consist of providing a general area to mount the sensor such as a slide, or the block may be specially shaped or configured to receive it e.g. in a groove or properly-dimensioned well.

The block and or sensor may in addition be adapted to form all or part of one wall of a flow channel, through which a liquid sample can flow in liquid contact with the metallised surface. An apparatus comprising such a flow channel forms one embodiment of the first aspect of the invention.

Preferably the metallised sensor surface is adapted or otherwise functionalised such as to facilitate the immobilisation of macromolecules which are capable of specifically binding biomolecules thereto. For instance the sensor may have a hydrophilic dextran surface. Antibodies may then be immobilised thereto in order to specifically bind antigenic analytes. Alternatively a polynucleotide probe may be immobilised for specifically binding a polynucleotide analytes.

Preferably the e.g. antibodies are bound only to discrete portions of surface in order to facilitate the detecting light which is scattered or emitted when an analyte is bound to thereto. These portions may then be visualised (and possibly further resolved) by the second detector as contrasting discrete bright areas against the darker portions of the surface which do not have macromolecules bound to them.

The surface may have greater then one type of macromolecule immobilised thereto for specifically binding greater then one type of antigen. The different types of e.g. antibody may be bound in known discrete areas in order to easily identify which antigen is being specifically bound.

In one further embodiment of the invention, the apparatus includes a second light source. This can be used to increase the intensity of the light scattered or emitted from the sensor surface when an analyte is bound thereto. Although this embodiment requires additional components, it has the advantage that the light source can be optimised (e.g. wavelength, angle of incidence against the sensor surface, intensity) for light scattering and/or fluorescence.

It may be desirable to locate the second light source such as to minimise the amount of stray light emitted therefrom which is detected by the second detector.

This may be done by locating the second light source such that light emitted therefrom travels along the same light path but in the opposite direction from the light from the first light source which is internally reflected from the sensor surface to the second detector, as is shown in the Figures below.

The light source(s) used can be selected without undue burden by those skilled in the art. In order to maximise intensity, and hence sensitivity, the or each light source may be a laser light source, or a light emitting diode.

In a second aspect of the invention there is disclosed a method of detecting an analyte in a sample comprising exposing the sensor surface of an apparatus as described above to the sample. The analyte may then be detected by the first or second detector.

For instance a soluble analyte in a sample may be detected by detecting the changes in the intensity of light internally reflected from the sensor surface. A particulate analyte in a sample may be detected by detecting the light scattered or emitted from the analytes bound to the sensor surface. Preferably the apparatus is arranged such that soluble or particulate analytes may be detected simultaneously.

The means adapted to secure the second detector may comprise a holder or clamp positioned and/or dimensioned to receive e.g. a video camera and associated optics, such that it can detect light scattered or emitted from the sensor surface. The holder or clamp may be moveable in a predetermined way to facilitate the function of the second detector when in place e.g. to allow focusing.

Preferably the means are adapted to secure the first detector such that it is capable of detecting light emitted at a predetermined angle, for example substantially normally, to the sensor surface.

The second detector of the apparatus may also be adapted such as to receive a second light source. The adaptation may be such that the second light source, when in place, is configured to minimise interference with the second detector by being directed away from it, as described above.

A fifth aspect is a sensor having a metallised surface and being adapted for the apparatus above, in particular so as to allow light emitted or scattered from the sensor surface to be transmitted to the first detector. The sensor may comprise a slide and the surface may be functionalised in discrete sections as described above.

While both SPR and particle detection by optical means are known in the prior art, the idea of modifying SPR apparatus (and, in particular, exploiting the existing light source and analyte binding site) to allow simultaneous detection of soluble and particulate analyte is a useful invention that is not obvious.

FIGURES

Figure 3A:
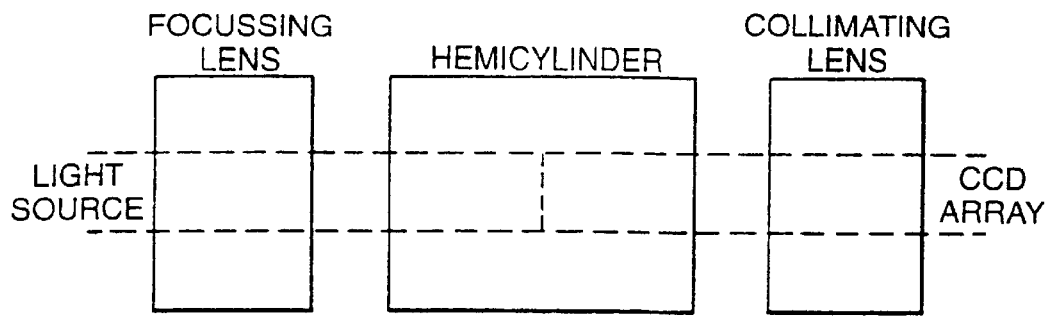
FIG. 3 Shows how the apparatus may be used to detect multiple analytes.

FIGS. 3(a) and (b) show the light source, hemicylinder (plus detection surface), and CCD array detector schematically.

Figure 3B:
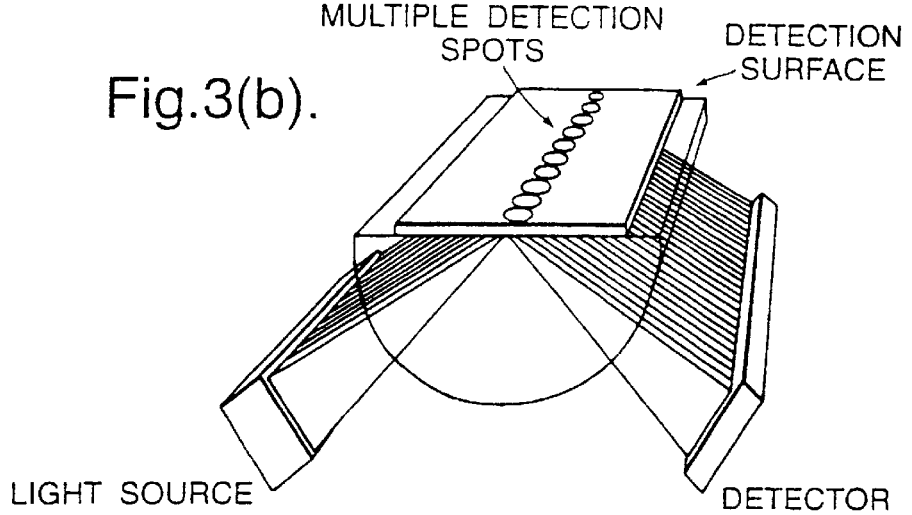
Figure 3C:
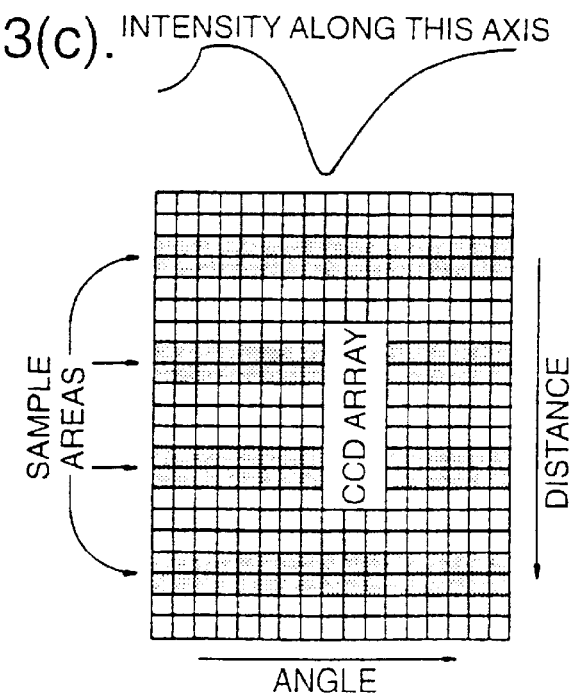

FIG. 3(c) shows a detail of the CCD array.

Figure 4:
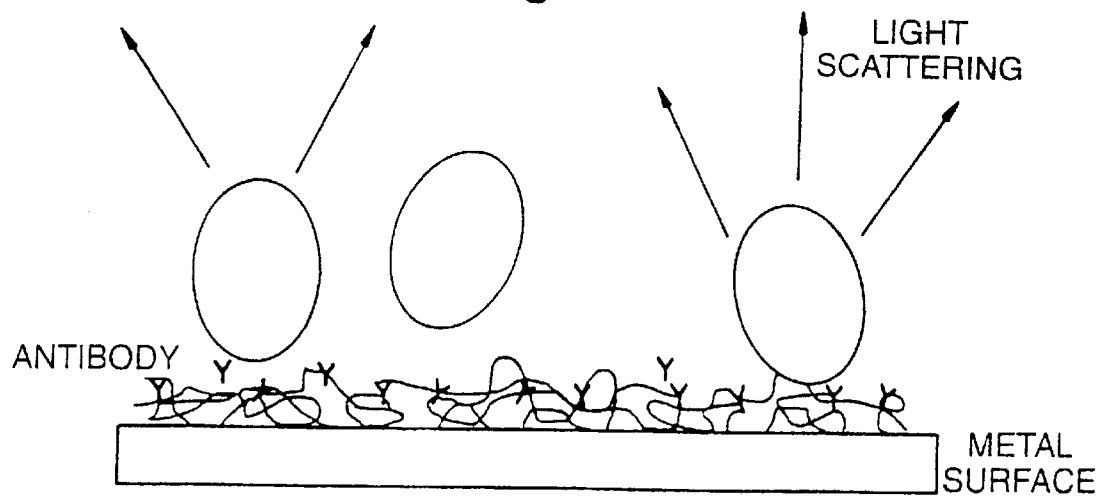

FIG. 4 Shows bound particles scattering light from the metallised detection surface of a hemicylinder sensor. The light can be detected by a video camera (not shown).

Figure 5:
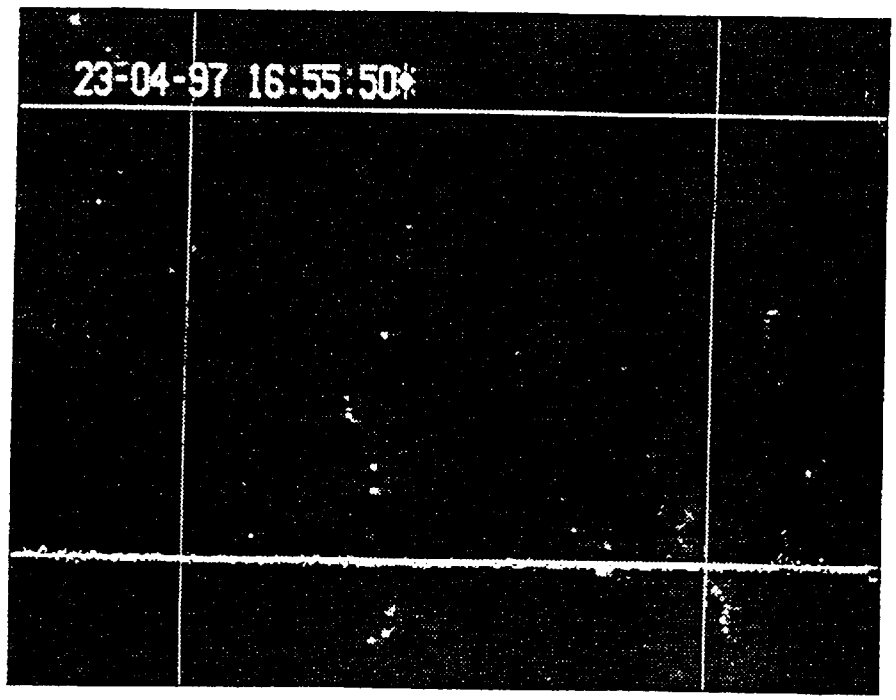

FIG. 5 shows scattering from bacterial particles above a silver surface: the points of light represent scattered light from *Erwinia herbicola*.

EXAMPLES

Example 1

Figure 1:
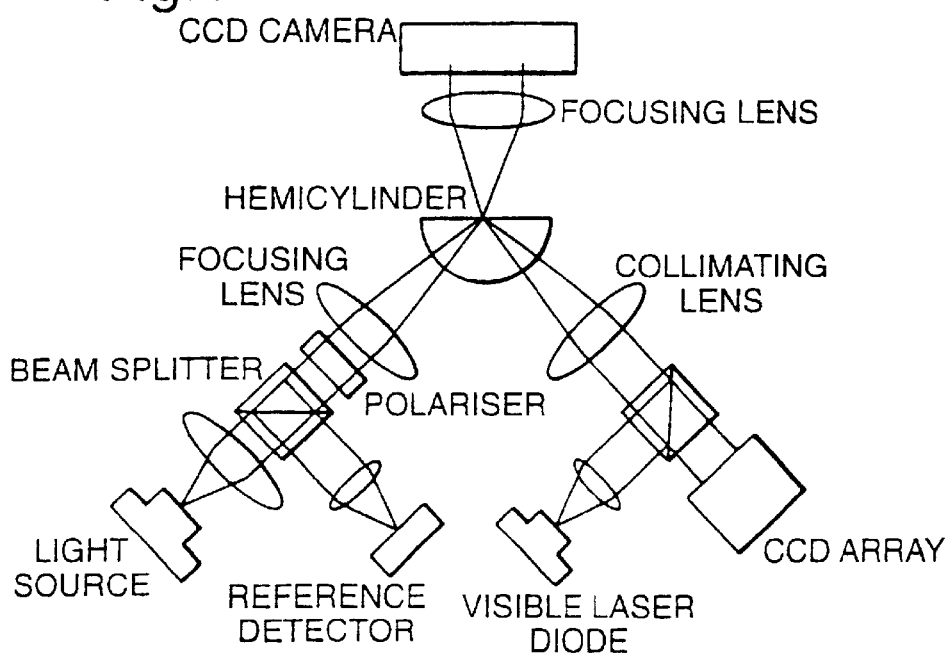
FIG. 1 Shows a schematic diagram of a surface plasmon resonance apparatus for detecting a soluble or a particulate analyte, as described in more detail in Example 1.
Figure 2:
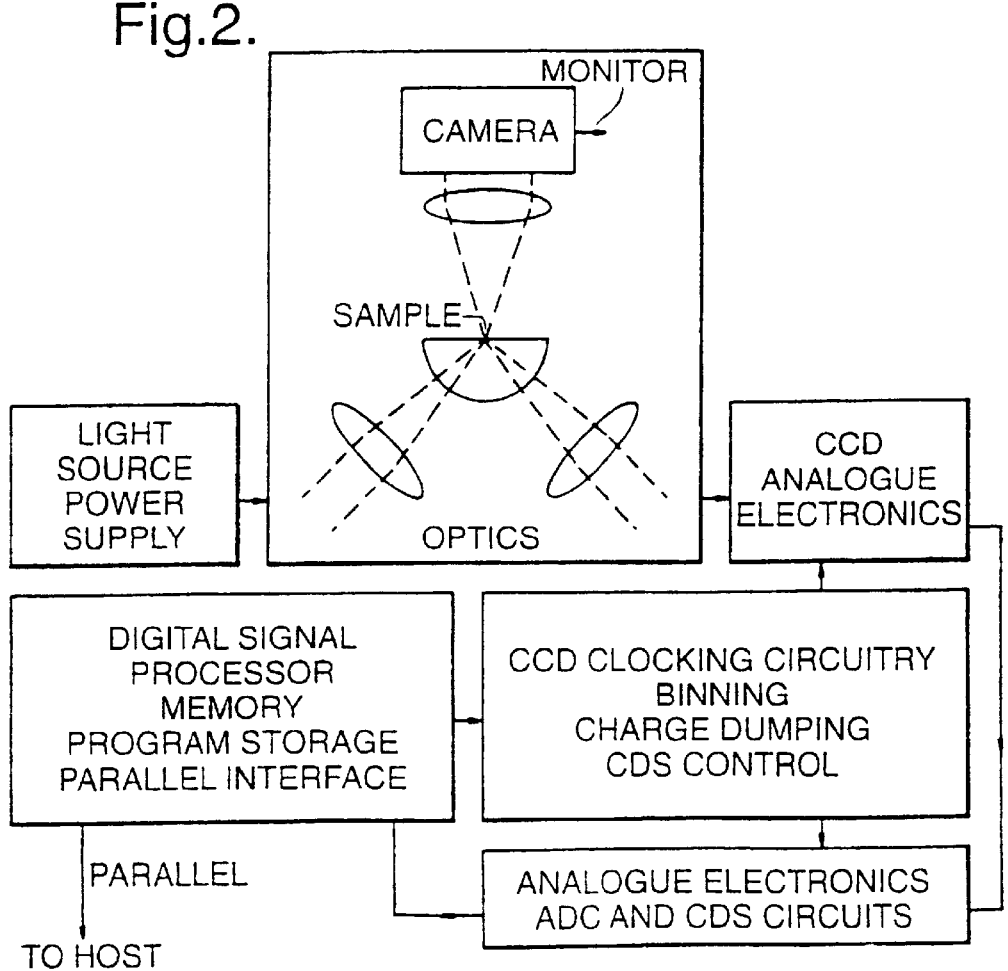
FIG. 2 Shows a block diagram of the complete instrument of Example 1.

Surface Plasmon Resonance Apparatus for Detecting a Soluble or a Particulate Analyte FIG. 1 Shows a schematic diagram of a surface plasmon resonance apparatus for detecting a soluble or a particulate analyte, such as could be constructed (in the light of the present disclosure) by those skilled in the art. A block diagram of the components of the apparatus is shown in FIG. 2.

This system may be rearranged if desired, for instance the polariser may be placed after the hemicylinder if required.

Considering FIG. 1, the light path to the first detector ('CCD Array') is from the light source at the left, through the beam splitter (which splits a portion to the reference detector), through a polariser and focusing lens, off the internal surface of the hemicylinder, through a collimating lens and into the CCD array.

The light path is shown schematically in FIG. 3(a). An extended collimated source may be used to illuminate the hemicylinder surface continuously over a range of incident angles, as shown in FIG. 3(b). The CCD array is composed of a pixelated array of individual light sensors, each detecting a different reflected angle or being used to detect a different sample analyte (in this case 4 different samples) as shown in FIG. 3(c). This allows the rapid monitoring without moving parts.

Considering FIG. 1, the light path to the second detector ('CCD camera') is from the light source at the left, through the beam splitter (which splits a portion to the reference detector), through a polariser and focusing lens and onto the hemicylinder.

The intensity is supplemented in this embodiment by light from the visible laser diode on the right which travels away from the CCD array and through the collimating lens on the right and onto the hemicylinder. The evanescent field generated on the upper, metallised, surface of the hemicylinder causes particles bound therein to scatter light as depicted in FIG. 4. The scattered light is focused through a lens and detected by the CCD camera.

Naturally if the particles were fluorescently labelled, using reagents (e.g. fluourescein) and methods well known to those skilled in the art, then the CCD camera could detect emitted light as the particles are excited by the evanescent field.

Devices according to Example 1 may be constructed based on existing SPR machines but having the additional components described above. The machines and components may be those available commercially. For instance the light source may advantageously be an edge emitting LED as used in fibre-optic communications (e.g. EG&G type S86018). A stabilised power supply may be used to minimise artefacts.

The sensor may be metal-coated microscope slide (or similar thickness dielectric) which is index matched onto the hemicylinder with fluid of similar refractive index. A portion of the hemicylinder may be ground off to accommodate the slide.

The CCD array (with 'pixels' about 20 $\mu m^2$) may be of a type developed for video use. Readout from CCD was accomplished by transferring a sample-area row to a readout or row register. Correlated Double Sampling (CDS) may be used to eliminate noise. The analog output can be passed to a digital signal processor via an ADC. A suitable processor is an Analog Devices ADSP-2105. This can communicate with an external host PC via a bi-directional parallel port.

The CCD video camera can be a conventional, commercially available, one e.g. as sold by Hamamatsu (Japan).

Example 2

Method of Use of Surface Plasmon Resonance Apparatus

In use, in order to correct for differences in source intensity along the collimated beam, a calibration can be carried out before the experiment. The sensor surface is then exposed to the sample(s). The host selects monitoring angles through using reflectivity vs. angle scans. Data is then acquired over a set time period and displayed by the host PC.

Example 3

Detection of Particulate Analyte Using the Second Detector

In order to illustrate the light scattering technique, a glass microscope slide was coated with silver for optimum surface plasmon resonance (48 nm). The slide was then mounted onto a glass hemicylindrical prism and illuminated with a 3 mW helium-neon laser. The slide was covered with a film of bacteria (*Erwinia herbicola*) at $1 \times 10^6$/ml in phosphate buffered saline solution. The bacteria were then allowed to adsorb onto the surface of the silver microscope slide.

The bacteria were then allowed to adsorb onto the surface of the silver microscope slide. The output from the CCD array above the SPR surface is a normal video output with 256 levels of brightness. Observation above the silver surface showed that initially all pixels on the CCD camera gave a low reading (1–20) and the surface appeared dark. As the bacteria approached the surface, the brightness increased for those pixels specifically aligned with the areas where the bacteria were on the surface. The maximum brightness level recorded from the light scattered by the bacteria at the surface was 230. The appearance of the surface was that of a dark background with bright spots associated with the bacteria on the surface (See FIG. 5).

As a control, a film of phosphate buffered saline without bacteria was used to cover the silver surface of a similar microscope slide. This time, no scattering from the surface was observed.

What is claimed is:

1. A surface plasmon resonance apparatus for detecting a soluble and, or a particulate analyte, the apparatus comprising:
    a sensor providing a metallised surface capable of binding the analyte;
    a light source capable of generating an evanescent wave at the sensor surface;
    a first detector comprising means for producing an image of the metallised surface derived from light scattered by analyte particles bound thereto and
    a second detector capable of detecting light from the light source which is internally reflected from the metallised surface.

2. Apparatus according to claim 1 where the first detector is a video camera.

3. Apparatus according to claim 1 where the first detector is a 2-dimensional diode array.

4. A method of detecting particulate analyte comprising:
    (a) binding the analyte to a sensor, said sensor comprising a metallised surface capable of binding the analyte;
    (b) providing a light source capable of generating an evanescent wave at the sensor surface;
    (c) imaging the metallised surface by means of light scattered by analyte particles bound to the metallised surface and
    (d) detecting light from the light source which light is internally reflected from the metallised surface.

* * * * *